United States Patent
Tarumoto et al.

(10) Patent No.: US 12,357,153 B2
(45) Date of Patent: Jul. 15, 2025

(54) RISING BASE AND ENDOSCOPE

(71) Applicant: HOYA CORPORATION, Tokyo (JP)

(72) Inventors: Tetsuya Tarumoto, Tokyo (JP); Reiko Takahashi, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 545 days.

(21) Appl. No.: 17/796,107

(22) PCT Filed: Feb. 16, 2021

(86) PCT No.: PCT/JP2021/005637
§ 371 (c)(1),
(2) Date: Jul. 28, 2022

(87) PCT Pub. No.: WO2021/199739
PCT Pub. Date: Oct. 7, 2021

(65) Prior Publication Data
US 2023/0080583 A1  Mar. 16, 2023

(30) Foreign Application Priority Data

Mar. 31, 2020  (JP) ................................. 2020-063683

(51) Int. Cl.
*A61B 1/00* (2006.01)
*A61B 1/012* (2006.01)

(52) U.S. Cl.
CPC ........ *A61B 1/0008* (2013.01); *A61B 1/00098* (2013.01); *A61B 1/00101* (2013.01); *A61B 1/012* (2013.01)

(58) Field of Classification Search
CPC ... A61B 1/0008; A61B 1/012; A61B 1/00098; A61B 1/00101
See application file for complete search history.

(56) References Cited

U.S. PATENT DOCUMENTS

| | | |
|---|---|---|
| 5,707,344 A | 1/1998 | Nakazawa et al. |
| 2016/0270633 A1 | 9/2016 | Iwasaka et al. |
| 2016/0270636 A1 | 9/2016 | Iwasaka et al. |
| 2018/0153377 A1 | 6/2018 | Kodama |

(Continued)

FOREIGN PATENT DOCUMENTS

| | | |
|---|---|---|
| CN | 107920720 A | 4/2018 |
| JP | 6157791 B2 | 7/2017 |
| JP | 2019-115562 A | 7/2019 |

(Continued)

OTHER PUBLICATIONS

Office Action issued in Japanese Application No. 2020-063683, dated Feb. 27, 2024, along with an English translation thereof.

(Continued)

*Primary Examiner* — Aaron B Fairchild
(74) *Attorney, Agent, or Firm* — GREENBLUM & BERNSTEIN, P.L.C.

(57) ABSTRACT

Provided are an elevator that can be reliably attached by a simple operation and an endoscope including the elevator. An elevator engages with and attached to an engagement end of a rotation shaft protruding from a distal end portion of the endoscope by being pushed in from a direction intersecting with an axial length direction, and is elevated according to rotation of the rotation shaft. A jig is connected to the elevator, and the jig has a grip portion that is gripped when the elevator is attached and can be separated after the attachment.

5 Claims, 6 Drawing Sheets

(56) References Cited

U.S. PATENT DOCUMENTS

2019/0117045 A1  4/2019  Hosogoe
2020/0390322 A1  12/2020 Saito

FOREIGN PATENT DOCUMENTS

WO  2018/016484 A1  1/2018
WO  2019/131836 A1  7/2019

OTHER PUBLICATIONS

Office Action issued in Chinese Application No. 202180020103.2, dated Oct. 14, 2024.
European Search Report issued in EP Application No. 21780549.8, dated Feb. 21, 2024.
International Search Report issued in International Bureau of WIPO Patent Application No. PCT/JP2021/005637, dated Mar. 30, 2021, along with an English translation thereof.

RISING BASE AND ENDOSCOPE

TECHNICAL FIELD

The present invention relates to an elevator and an endoscope provided with the elevator.

BACKGROUND ART

An endoscope is a medical device that enables observation and treatment of a desired portion by being inserted into a body cavity of a subject. The treatment by the endoscope is executed by causing a treatment tool such as a piercing needle or forceps to pass through an insertion tube to be inserted into the body cavity and causing the treatment tool to protrude from a distal end portion of the insertion tube. The distal end portion of the insertion tube is provided with an elevator for elevating the treatment tool and changing a direction of the treatment tool. The elevator is attached to face a lead-out port of the treatment tool and swings around an axis intersecting with a lead-out direction to elevate the treatment tool.

An endoscope described in Patent Literature 1 includes a detachable elevator, and enables implementation of reliable treatment including a mount position of the elevator by removing the elevator at the time of cleaning, disinfection, and sterilization treatment required after use.

CITATION LIST

Patent Literature

Patent Literature 1: JP 6157791 B

SUMMARY OF INVENTION

Technical Problem

In Patent Literature 1, the elevator is attached by a procedure of pushing the elevator into an end portion of a rotation shaft protruding in a distal end portion of the endoscope from a direction intersecting with an axial length direction and causing the elevator to engage with the rotation shaft. However, the elevator is a minute-size component that can be incorporated into the distal end portion of the endoscope, and it is difficult to reliably attach the elevator by gripping the elevator with fingers. In addition, in a case where a gripper such as a pair of tweezers is used, there is a possibility that an observation window, an illumination window, and the like provided at the distal end portion of the endoscope are damaged by collision with the gripper, and careful attachment work is forced.

An object of the present disclosure is to provide an elevator that can be reliably attached by a simple operation and an endoscope including the elevator.

Solution to Problem

An elevator according to the present disclosure includes, in the elevator engaging with and attached to an end portion of a rotation shaft protruding from a distal end portion of an endoscope by being pushed in from a direction intersecting with an axial length direction, and configured to be elevated according to rotation of the rotation shaft, a jig having a grip portion that is gripped at a time of attachment to the rotation shaft, the jig being connected in a separable manner after the attachment.

Further, an anti-slip layer is provided on a surface of the jig including the grip portion.

Further, the jig is connected in a foldably removable manner.

Further, the jig is connected by screwing.

Further, the jig is connected by magnetic adhesion.

Furthermore, an endoscope according to the present disclosure is an endoscope including an elevator incorporated in a distal end portion of an insertion tube, in which the elevator engages with and is attached to an end portion of a rotation shaft protruding from the distal end portion by being pushed in from a direction intersecting with an axial length direction, and includes a jig having a grip portion that is gripped at a time of attachment to the rotation shaft, the jig being connected in a detachable manner after the attachment.

Advantageous Effects of Invention

According to the present disclosure, it is possible to provide an elevator that can be reliably attached by a simple operation and an endoscope including the elevator.

DESCRIPTION OF EMBODIMENTS

Hereinafter, embodiments of the present disclosure will be described with reference to the drawings.

First Embodiment

Figure 1:
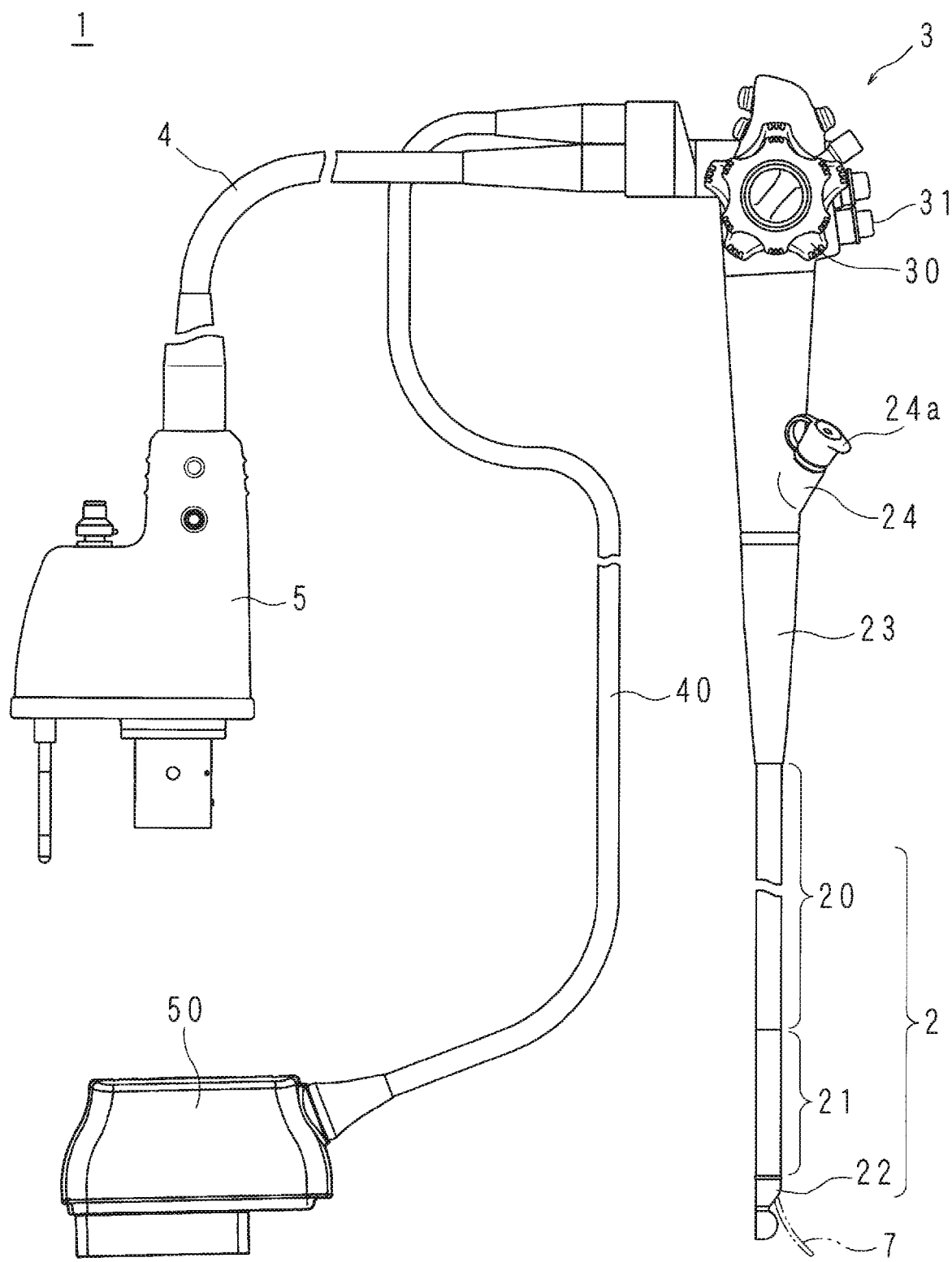
FIG. 1 is an exterior view of an endoscope.

FIG. 1 is an exterior view of an endoscope. As illustrated in the drawing, an endoscope 1 includes an insertion tube 2, an operation unit 3, a universal tube 4, and a connector unit 5. The insertion tube 2 is a portion to be inserted into a body cavity, and includes a long soft portion 20 and a distal end portion 22 connected to one end of the soft portion 20 via a bending portion 21. The other end of the soft portion 20 is connected to the operation unit 3 via a cylindrical connection portion 23. The universal tube 4 has one end connected to the operation unit 3 and extends in a direction different from the insertion tube 2, and the connector unit 5 is connected to the other end of the universal tube 4, The endoscope 1 is used by being connected to a processor device (not illustrated) by the connector unit 5.

The illustrated endoscope 1 is configured as an endoscopic ultrasonography including an ultrasonic probe 29 (see FIG. 2) at the distal end portion 22, and further includes a connection tube 40 arranged in parallel with the universal tube 4 and an ultrasonic connector unit 50 linked to an end portion of the connection tube 40.

The operation unit 3 is provided so as to be gripped by a user to perform various operations, and includes a plurality of operation knobs 30, a plurality of operation buttons 31, and the like, One operation knob 30 is connected to the bending portion 21 by a wire (not illustrated) passing through the inside of each of the connection portion 23 and the soft portion 20. The bending portion 21 is bent by the operation of the corresponding operation knob 30, so that the direction of the distal end portion 22 inserted in the body cavity is changed.

Further, another operation knob 30 is connected to the elevator 6 (see FIG. 2) incorporated in the distal end portion 22 by a wire (not illustrated) passed through the connection portion 23, the soft portion 20, and the bending portion 21. The elevator 6 operates as will be described below by the operation of the operation knob 30.

The connection portion 23 is provided with a treatment tool insertion port 24 into which a treatment tool 7 such as a piercing needle or forceps is inserted. The treatment tool insertion port 24 communicates with a lead-out port 25 (see FIG. 2) provided in the distal end portion 22 by a treatment tool channel (not illustrated) extending through the connection portion 23, the soft portion 20, and the bending portion 21. The treatment tool 7 is used by being inserted into the treatment tool insertion port 24, passing through the treatment tool channel and the lead-out port 25, and protruding from the distal end portion 22. In FIG. 1, the treatment tool 7 protruding from the distal end portion 22 is illustrated by the two-dot chain line. A sealing plug 24a in FIG. 1 seals the treatment tool insertion port 24 when the treatment tool 7 is not used.

Figure 2:
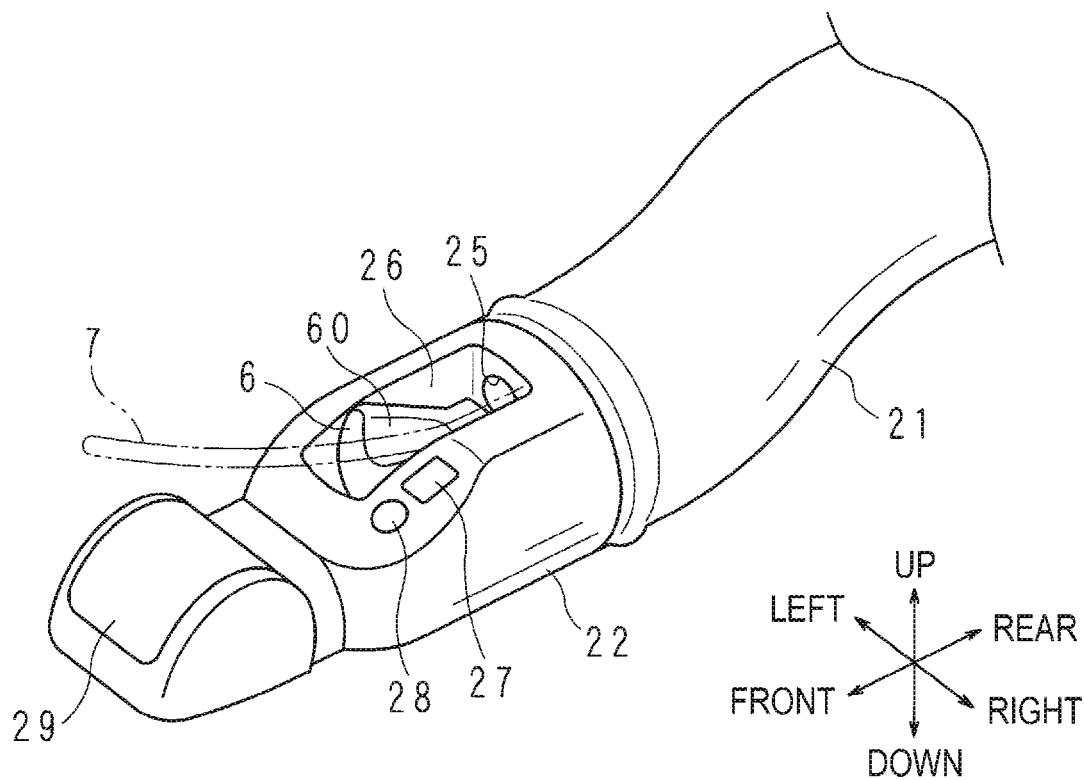
FIG. 2 is a perspective view of a distal end portion of the endoscope.

FIG. 2 is a perspective view of the distal end portion 22 of the endoscope 1. In the following description, up and down, left and right, and front and rear illustrated by the arrows in FIG. 2 are used.

The distal end portion 22 is a hard resin-made cylindrical body coaxially fixed to a front end portion of the bending portion 21, and includes a housing portion 26 that houses the above-described elevator 6. The housing portion 26 is a recess provided in an upper surface of the distal end portion 22 with a rectangular opening that is long in a front-rear direction, and the above-described lead-out port 25 of the treatment tool 7 opens in a rear inner surface continuing to the bending portion 21. The elevator 6 is attached to face the lead-out port 25 as described below, and is housed in the housing portion 26. A recess 60 is provided in the upper surface of the elevator 6, and the treatment tool 7 led out through the lead-out port 25 is guided by the recess 60 as illustrated by the two-dot chain line in FIG. 2 and protrudes to an outside of the distal end portion 22 through an upper opening of the housing portion 26.

The upper surface of the distal end portion 22 is inclined with a front side downward, and an observation window 27 and an illumination window 28 are provided side by side in a front-rear direction in a right inclined surface of the housing portion 26. An image sensor (not illustrated) such as a complementary metal oxide semiconductor (CMOS) is provided inside the observation window 27, and a light emitting end of a light guide (not illustrated) that guides illumination light is provided inside the illumination window 28, respectively, for example, so that an observation site facing the observation window 27 can be imaged and observed under the illumination light from the illumination window 28.

Furthermore, the ultrasonic probe 29 is linked to a front portion of the distal end portion 22, and an inside of a superficial tissue can also be observed by applying the ultrasonic probe 29 to the observation site to acquire an ultrasonic image.

Figure 3:
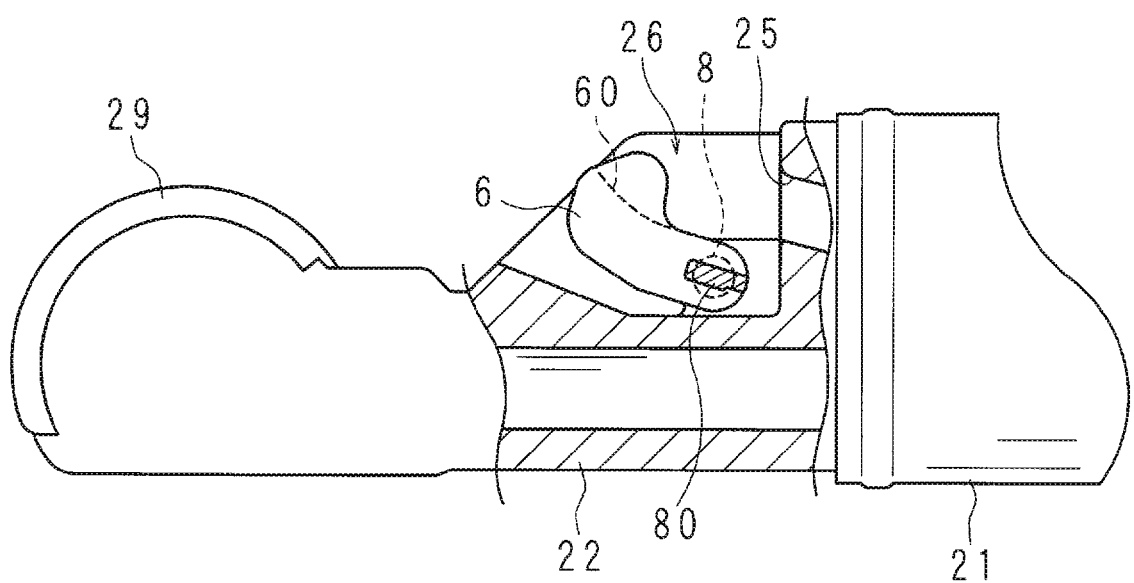
FIG. 3 is a side view illustrating a part of the distal end portion in a broken manner.

FIG. 3 is a side view illustrating a part of the distal end portion 22 in a broken manner, and schematically illustrates a mount mode of the elevator 6. A rotation shaft 8 is pivotally supported on a left-side (depth-side in the drawing) inner wall of the housing portion 26 that houses the elevator 6. The rotation shaft 8 is connected to the operation unit 3 by the above-described wire, and rotates around an axis intersecting with the paper surface by the operation of the corresponding operation knob 30, The elevator 6 is a resin-made block having elasticity, and has a base portion engaged with and attached to an engagement end 80 of the rotation shaft 8 protruding inside the housing portion 26. The elevator 6 swings so as to move up and down a distal end side provided with the recess 60 according to rotation of the rotation shaft 8, and changes the direction of the treatment tool 7 guided by and protruding from the recess 60.

Figure 4A:
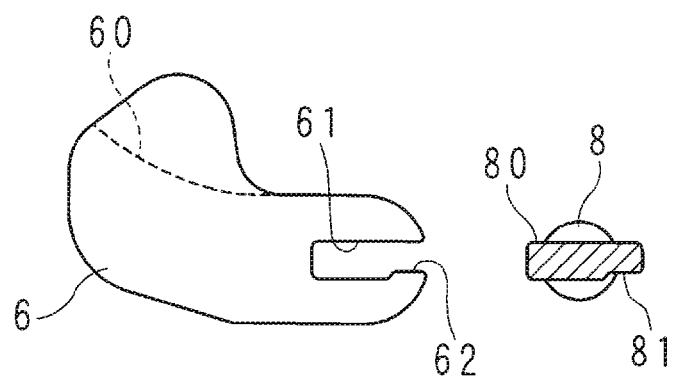
FIG. 4A is an explanatory view of a procedure of mounting an elevator.
Figure 4B:
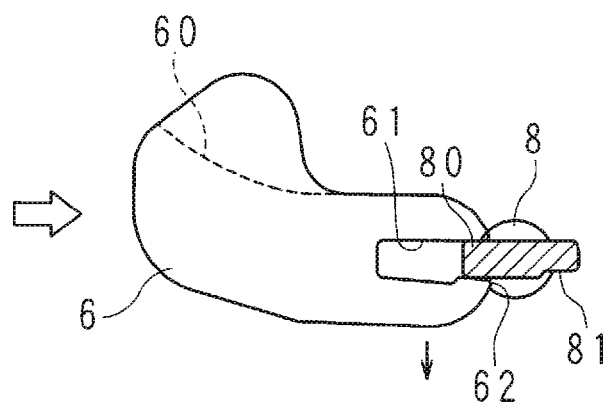
FIG. 4B is an explanatory view of the procedure of mounting an elevator.

FIGS. 4A and 4B are explanatory views of a procedure of mounting the elevator 6. The engagement end 80 of the rotation shaft 8 has a rectangular cross section as illustrated in the drawing, and a recess 81 is provided in an end portion on one side in a longitudinal direction. An engagement groove 61 having a shape corresponding to the engagement end 80 is provided in the base portion of the elevator 6, and a projection 62 corresponding to the recess 81 is provided on an opening-side end portion of the engagement groove 61, The mounting of the elevator 6 is executed by a procedure of causing the opening side of the engagement groove 61 to face the other side of the engagement end 80 as illustrated in FIG. 4A, and applying a pushing force in a direction intersecting with the axial length direction of the rotation shaft 8 as illustrated by the outlined arrow in FIG. 4B.

As illustrated in FIG. 4B, the elevator 6 is pushed into the engagement end 80 with expansion deformation of the engagement groove 61, and the projection 62 and the recess 81 are engaged by elastic recovery at a terminal end, whereby the elevator 6 is attached as illustrated in FIG. 3. Here, the elevator 6 is a small-sized component incorporated into the housing portion 26 of the distal end portion 22, and as described above, it is difficult to grip and attach the elevator 6 with an existing gripper such as fingers or tweezers.

Figure 5:
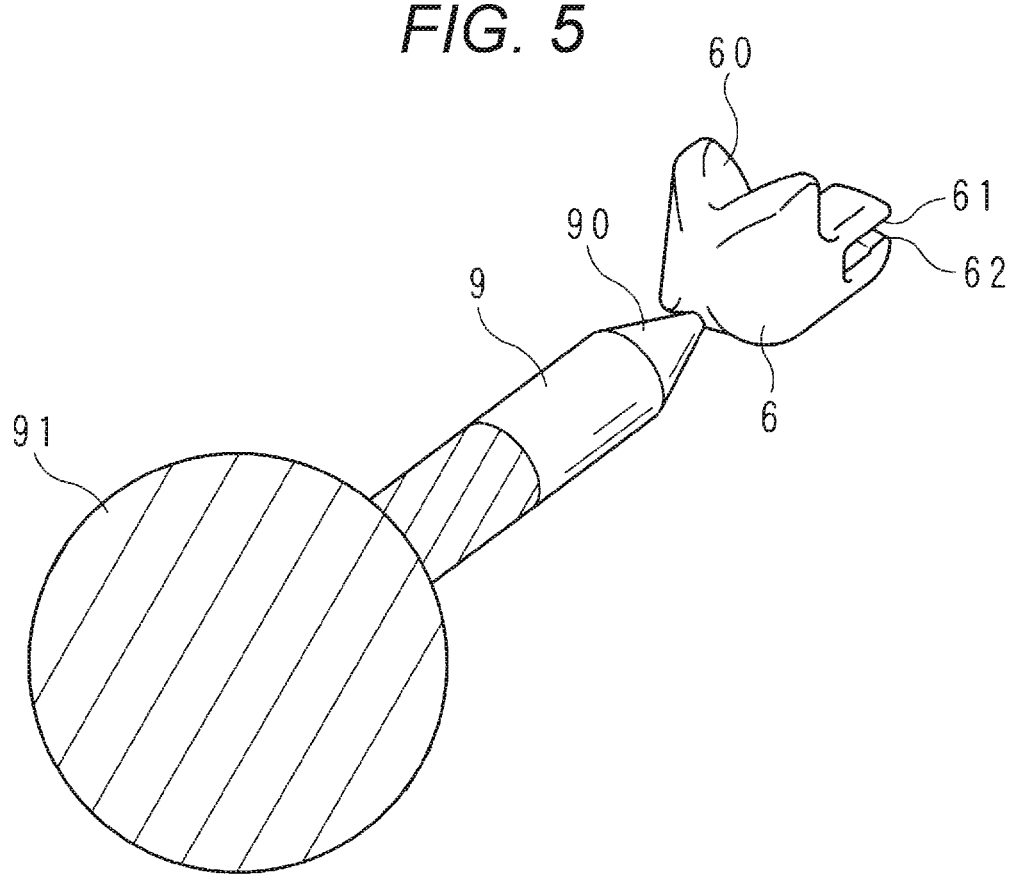
FIG. 5 is a perspective view illustrating a state before attachment of the elevator according to the first embodiment.

FIG. 5 is a perspective view illustrating a state before attachment of the elevator 6 according to the first embodiment. A jig 9 to be used at the time of the above-described mounting is connected to the elevator 6 illustrated in this drawing. The jig 9 is a resin-made round rod, and is provided with a connection portion 90 that is continuously reduced in diameter toward an end portion on one side, and a grip portion 91 having a spherical shape with a large diameter on the other side.

In such a jig 9, a distal end having a small diameter of the connection portion 90 is fixed to a distal end-side end surface of the elevator 6, and is connected so as to be aligned on the same line as the engagement groove 61 provided in the base portion of the elevator 6. This connection may be implemented by integrally molding the jig 9 and the elevator 6, or may be implemented by bonding the connection portion 90 of the separately provided jig 9 to the end surface of the elevator 6.

Figure 6A:
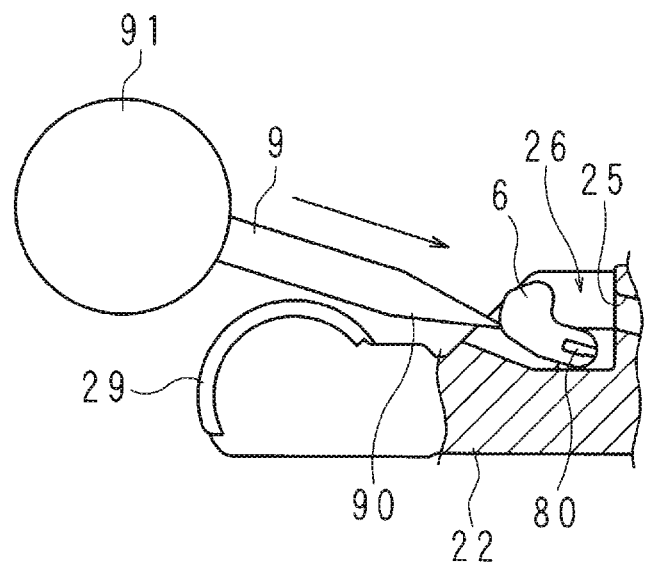
FIG. 6A is an explanatory view of a procedure of mounting the elevator illustrated in FIG. 5.
Figure 6B:
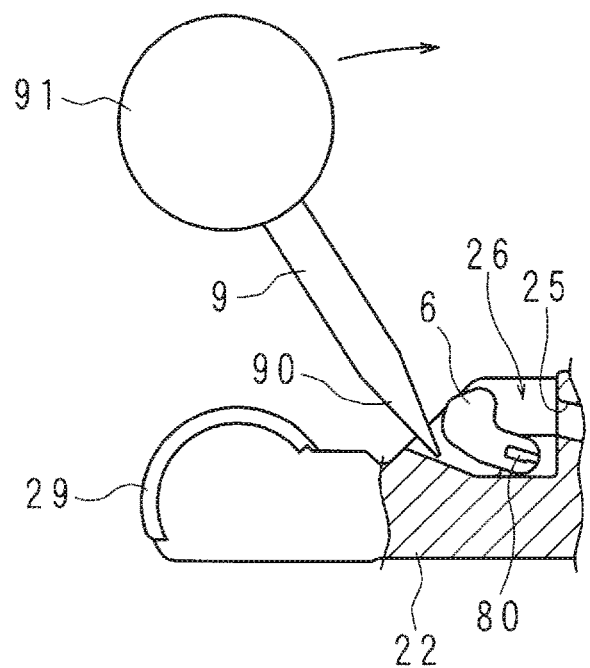
FIG. 6B is an explanatory view of the procedure of mounting the elevator illustrated in FIG. 5.

FIGS. 6A and 6B are explanatory views of a procedure of mounting elevator 6 illustrated in FIG. 5. The elevator 6 is attached by a procedure of positioning the elevator with respect to the engagement end 80 protruding in the housing portion 26, as described above, and then applying the force to push the elevator in the direction illustrated by the arrow in FIG. 6A. Since the jig 9 is connected to the elevator 6 illustrated in FIG. 5 and the jig 9 has the grip portion 91 on an opposite side of the connection portion 90 fixed to the elevator 6, the above-described pushing in to the engagement end 80 can be easily performed by gripping the grip portion 91 with fingers. Further, since the jig 9 is connected so as to be aligned on the same line as the engagement groove 61 engaged with the engagement end 80 and extends in parallel with the pushing direction, the jig 9 can reliably perform the pushing in to the engagement end 80.

The grip portion 91 of the jig 9 is not limited to the spherical shape illustrated in FIG. 5, and can have an appropriate shape as long as it has a size that allows easy gripping. In addition, the jig 9 is provided with an anti-slip layer on a surface including the grip portion 91 in order to prevent slippage at the time of pushing. In FIG. 5, an example of a formation range of the anti-slip layer is hatched. The anti-slip layer is desirably made of a soft material such as silicone rubber or urethane. As a result, it is possible to prevent damage to other portions that may come into contact in the process of pushing, particularly, the ultrasonic probe 29.

After the above attachment, the jig 9 is foldably removed by applying a bending force in a direction indicated by the arrow in FIG. 6B, and separated and removed from the elevator 6. Since the jig 9 is connected to the elevator 6 at the distal end having a small diameter of the connection portion 90, and stress due to the application of the bending force is concentrated on the connection portion, the jig 9 can be reliably foldably removed with a slight fold mark left on the end surface of the elevator 6.

Second Embodiment

Figure 7:
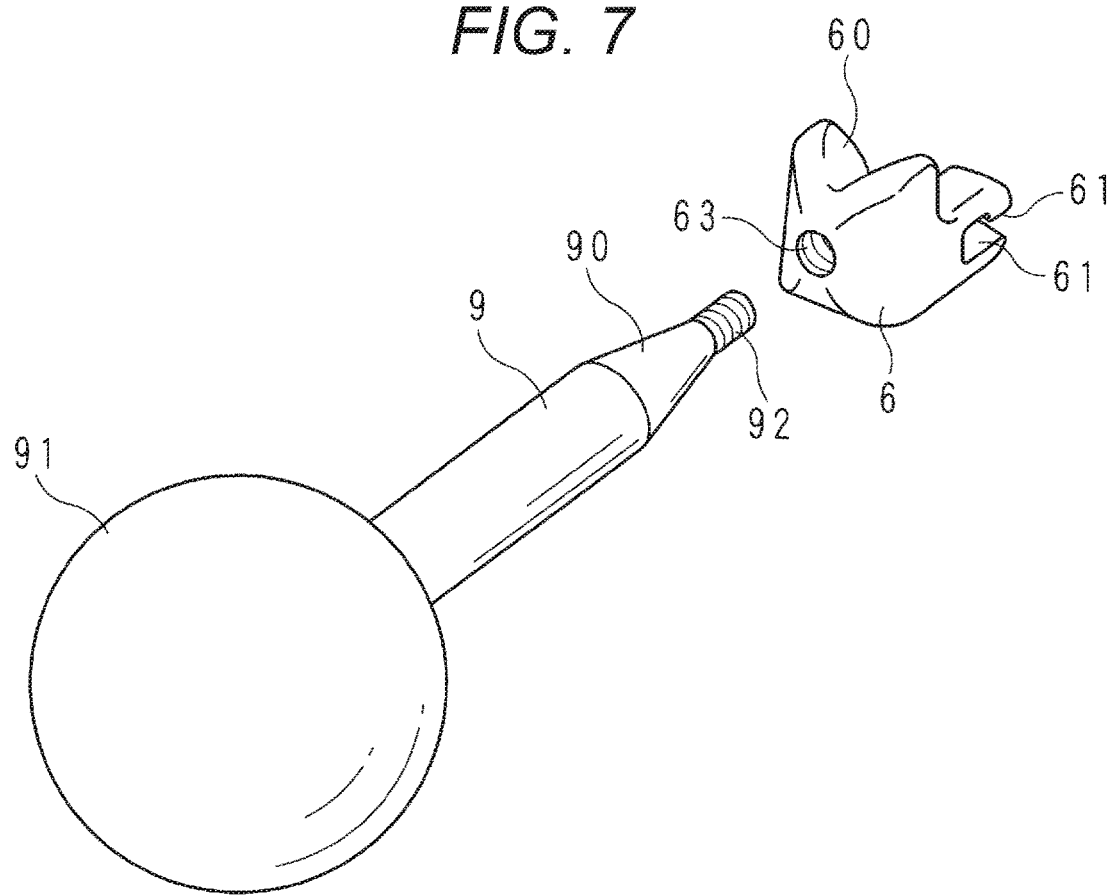
FIG. 7 is a perspective view illustrating a state before attachment of an elevator according to a second embodiment.

FIG. 7 is a perspective view illustrating a state before attachment of an elevator 6 according to a second embodiment. A jig 9 to be used at the time of the above-described mounting is connected to the elevator 6 illustrated in this drawing. The jig 9 is a resin-made round rod, and is provided with a connection portion 90 on one side and a grip portion 91 on the other side, as in the first embodiment. Unlike the first embodiment, a screw shaft 92 having a male screw formed in an outer periphery protrudes from a distal end of the connection portion 90.

Meanwhile, a screw hole 63 having a female screw formed in an inner periphery is formed in a distal end-side end surface of the elevator 6, and the jig 9 is connected to the elevator 6 by screwing the screw shaft 92 into the screw hole 63. As in the first embodiment, the elevator 6 to which the jig 9 is connected can be easily and reliably attached by gripping the grip portion 91. Note that it is desirable to provide a similar a slip layer to the first embodiment on a surface of the jig 9.

After the attachment, the jig 9 is separated from the elevator 6 and removed by applying a rotational force around an axis to release the screwing between the screw shaft 92 and the screw hole 63. The separated jig 9 can be reused for attaching another elevator 6 having the screw hole 63, and can also be used for removing the elevator 6 after use of the endoscope 1.

Third Embodiment

Figure 8:
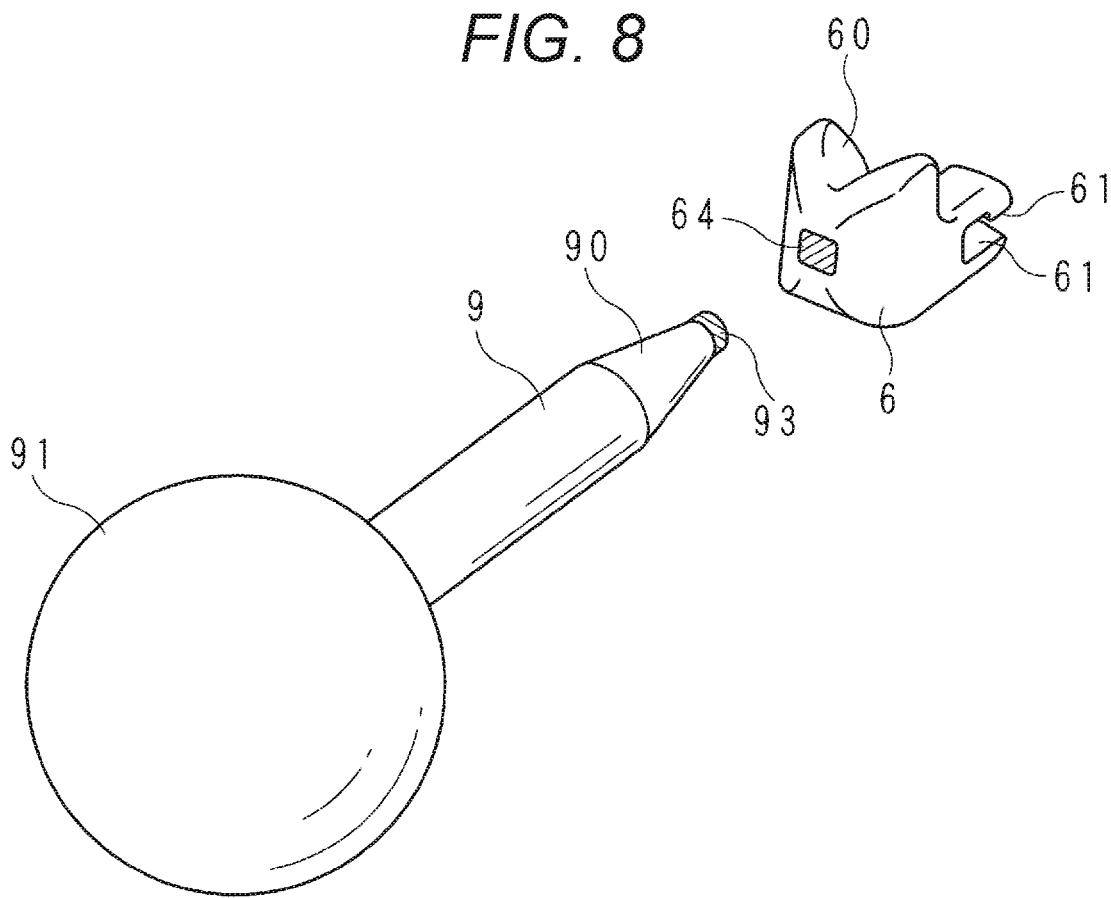
FIG. 8 is a perspective view illustrating a state before attachment of an elevator according to a third embodiment.

FIG. 8 is a perspective view illustrating a state before attachment of an elevator 6 according to a third embodiment. A jig 9 to be used at the time of the above-described mounting is connected to the elevator 6 illustrated in this drawing. The jig 9 is a resin-made round rod, and is provided with a connection portion 90 on one side and a grip portion 91 on the other side, as in the first embodiment. Unlike the first embodiment, a magnet 93 is fixed to a distal end of the connection portion 90.

On the other hand, a connection piece 64 made of a magnetic metal is fixed to a distal end-side end surface of the elevator 6, and the jig 9 is connected to the elevator 6 by causing the magnet 93 at the distal end to magnetically adhering to the connection piece 64. As in the first embodiment, the elevator 6 to which the jig 9 is connected can be easily and reliably attached by
gripping the grip portion 91. Note that it is desirable to provide a similar anti-slip layer to the first embodiment on a surface of the jig 9.

After attachment, a tensile force is applied to the jig 9 in an axial length direction and the jig 9 is separated and removed from the elevator 6 by releasing magnetic adhesion of the magnet 93 and the connection piece 64. The separated jig 9 can be reused for mounting another elevator 6 having the connection piece 64. The connection piece 64 may be embedded and installed in the elevator 6 so as to face the distal end-side surface of the elevator 6.

Fourth Embodiment

The connection position of the jig 9 is not limited to the position described in the above-described first to third embodiment, and can be set to an appropriate position where the pushing force can be applied, other than a position where contact with the treatment tool 7 is assumed and a position where interference with the inner surface of the housing portion 26 is assumed. Further, the shape of the jig 9 is not limited to the shapes illustrated in the first to third embodiments.

Figure 9:
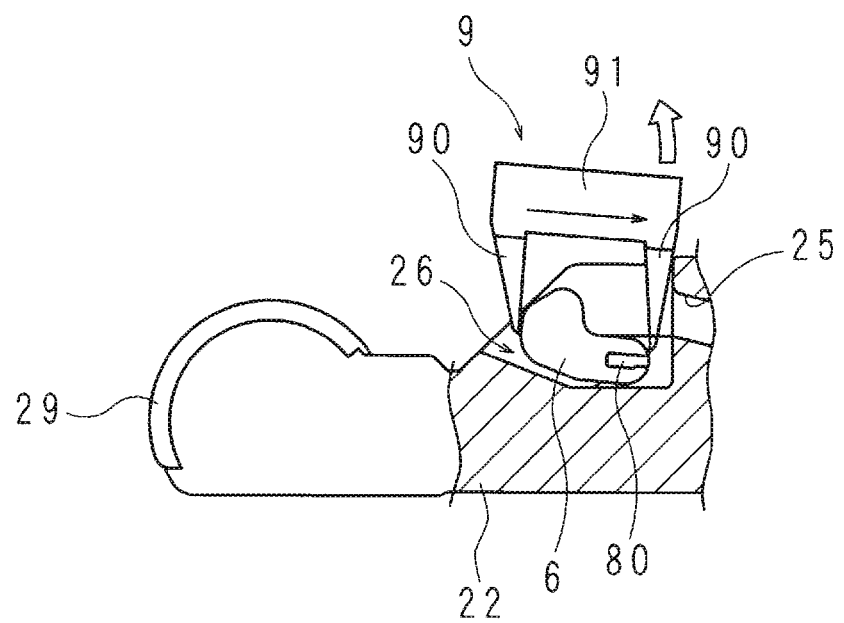
FIG. 9 is an explanatory view of a procedure of mounting an elevator according to a fourth embodiment.

FIG. 9 is an explanatory view of a procedure of mounting an elevator 6 according to a fourth embodiment, A jig 9 to be used at the time of mounting is connected to an illustrated elevator 6. The jig 9 includes a grip portion 91 having a rod shape and two connection portions 90 protruding in the same direction from both end portions of the grip portion 91. The connection portions 90 are continuously reduced in diameter toward end portions, and the jig 9 and the elevator 6 are connected by having a distal end having a small diameter of one connection portion 90 fixed to a distal end-side end surface of the elevator 6 and a distal end having a small diameter of the other connection portion 90 fixed to a proximal end-side end surface of the elevator 6, respectively. This connection may be implemented by integrally molding the jig 9 and the elevator 6, or may be implemented by bonding or welding the connection portions 90 of the separately provided jig 9 to the elevator 6.

Similarly to the first embodiment, the elevator 6 having the above configuration is attached by a procedure of gripping the grip portion 91 of the jig 9, inserting the grip portion into a housing portion 26, positioning the elevator with respect to an engagement end 80 protruding into the housing portion 26, as described above, then applying a force to push the elevator in a direction illustrated by the arrow in FIG. 9.

After the above attachment, the jig 9 is foldably removed by applying a bending force in a direction indicated by the outlined arrow in FIG. 9, and separated and removed from the elevator 6. Since the jig 9 is connected to the elevator 6 at the distal ends having a small diameter of the connection portions 90, and stress due to the application of the bending force is concentrated on the connection end portions, the jig 9 can be reliably foldably removed.

Note that the embodiments disclosed herein are exemplary in all respects, and it should be considered that the embodiments are not restrictive. The scope of the present invention is defined not by the above-described meaning but by claims, and is intended to include all modifications within significance and a scope equivalent to the claims.

REFERENCE SIGNS LIST

1 Endoscope
6 Elevator
8 Rotation shaft
9 Jig
80 Engagement end
91 Grip portion

The invention claimed is:

1. An endoscopic assembly comprising:
an elevator in the proximal direction removably engageable with an end portion of a rotation shaft protruding from a distal end portion of an endoscope by being pushed in a proximal direction of the elevator intersecting with an axial length direction of the endoscope, the elevator configured to be elevated according to rotation of the rotation shaft; and
a jig having a grip configured to be gripped by a user, the jig configured to be connectable to the elevator when attaching the elevator to the rotation shaft, the jig further configured to be removable from to the elevator after the attachment of the elevator to the rotation shaft.

2. The endoscopic assembly according to claim 1, further comprising anti-slip layer on a surface of the jig including the grip.

3. The endoscopic assembly according to claim 1, wherein the jig is configured to be connectable to the elevator in a foldably removable manner.

4. The endoscopic assembly according to claim 1, wherein the jig is configured to be connectable to the elevator by screwing.

5. The endoscopic assembly according to claim 1, wherein the jig is configured to be connectable to the elevator by magnetic adhesion.

* * * * *